US011293909B2

(12) United States Patent
Suzuki et al.

(10) Patent No.: US 11,293,909 B2
(45) Date of Patent: Apr. 5, 2022

(54) MANAGEMENT METHOD AND MANAGEMENT DEVICE

(71) Applicant: SINTOKOGIO, LTD., Nagoya (JP)

(72) Inventors: Takashi Suzuki, Nukata-gun (JP); Keisuke Takayanagi, Nukata-gun (JP)

(73) Assignee: SINTOKOGIO, LTD., Aichi (JP)

(*) Notice: Subject to any disclaimer, the term of this patent is extended or adjusted under 35 U.S.C. 154(b) by 22 days.

(21) Appl. No.: 16/903,797

(22) Filed: Jun. 17, 2020

(65) Prior Publication Data

US 2021/0063373 A1 Mar. 4, 2021

(30) Foreign Application Priority Data

Aug. 29, 2019 (JP) .............................. JP2019-157296

(51) Int. Cl.
*G01N 33/00* (2006.01)
*G01S 5/00* (2006.01)
*H04W 4/029* (2018.01)
*G04F 3/00* (2006.01)
*G06F 1/16* (2006.01)

(52) U.S. Cl.
CPC ..... *G01N 33/0075* (2013.01); *G01N 33/0036* (2013.01); *G01N 33/0062* (2013.01); *G01S 5/0027* (2013.01); *H04W 4/029* (2018.02); *G04F 3/00* (2013.01); *G06F 1/163* (2013.01)

(58) Field of Classification Search
CPC ........... G01N 33/0075; G01N 33/0036; G01N 33/0062; H04W 4/029; G01S 5/0027
USPC ........................................................ 340/632
See application file for complete search history.

(56) References Cited

U.S. PATENT DOCUMENTS

| 10,527,722 | B2 | 1/2020 | Carlson et al. |
| 2004/0256474 | A1 | 12/2004 | Park et al. |
| 2006/0180676 | A1 | 8/2006 | Park et al. |
| 2006/0216200 | A1 | 9/2006 | Nagatomo et al. |
| 2008/0243305 | A1 | 10/2008 | Lee et al. |
| 2011/0163892 | A1* | 7/2011 | Groves .............. G01N 33/0075 340/901 |

(Continued)

FOREIGN PATENT DOCUMENTS

| JP | 2005-016931 A | 1/2005 |
| JP | 2008-254167 A | 10/2008 |
| JP | 2013-032926 A | 2/2013 |

OTHER PUBLICATIONS

Office Action for U.S. Appl. No. 16/899,798 dated Apr. 14, 2021.

(Continued)

*Primary Examiner* — Kerri L McNally
(74) *Attorney, Agent, or Firm* — Harness, Dickey & Pierce, P.L.C.

(57) ABSTRACT

A management method for managing a working environment of a worker who moves in a workplace includes: a receiving process of receiving, from a mobile device worn by the worker, (i) a measurement value that has been obtained in a measuring process of carrying out environment measurement and (ii) positional information indicative of a location at which the measuring process has been carried out; and a making process of making, with reference to the measurement value and the positional information, a map that shows spatial distribution of measurement values in the workplace.

9 Claims, 8 Drawing Sheets

(56) References Cited

U.S. PATENT DOCUMENTS

| | | |
|---|---|---|
| 2014/0114561 A1* | 4/2014 | Pakzad ................ G01C 21/206 |
| | | 701/410 |
| 2014/0207282 A1* | 7/2014 | Angle .................... G05B 15/02 |
| | | 700/257 |
| 2016/0352784 A1 | 12/2016 | Oh |
| 2017/0041750 A1 | 2/2017 | Jose et al. |
| 2017/0156189 A1 | 6/2017 | Jayawardena et al. |
| 2018/0050171 A1 | 2/2018 | Tabert et al. |
| 2018/0252942 A1* | 9/2018 | Gamliel ................ G02C 7/027 |
| 2019/0107469 A1 | 4/2019 | Han et al. |
| 2021/0055272 A1 | 2/2021 | Cho |

OTHER PUBLICATIONS

Office Action for U.S. Appl. No. 16/899,798 dated Sep. 2, 2021.
Notice of Allowance for U.S. Appl. No. 16/899,798 dated Dec. 15, 2021.

* cited by examiner

MANAGEMENT METHOD AND MANAGEMENT DEVICE

This Nonprovisional application claims priority under 35 U.S.C. § 119 on Patent Application No. 2019-157296 filed in Japan on Aug. 29, 2019, the entire contents of which are hereby incorporated by reference.

TECHNICAL FIELD

The present invention relates to a management method and a management device, each of which is for managing a working environment of a worker who moves in a workplace.

BACKGROUND ART

Generally, environment measurement is carried out with use of handy apparatuses and various sensors such as fixed sensors. Note, here, that, in a case where environment measurement is merely carried out with use of various sensors, it is possible to obtain measurement values at locations at which the environment measurement has been carried out, but it is not possible to intuitively and easily understand environmental conditions in large regions. For this reason, a technique of making a map that shows spatial distribution of measurement values that have been obtained by environment measurement has been developed.

For example, each of Patent Literatures 1 and 2 discloses such a technique that (a) a robot configured to move in a room carries out environment measurement with use of a sensor and (b) a server (i) receives, from the robot, a measurement value that has been obtained by the environment measurement and (ii) makes a map that shows spatial distribution of measurement values.

Patent Literature 3 discloses such a technique that a vehicle having a map making system (i) carries out environment measurement while moving in a city or moving along a national road, a prefectural road, and the like and (ii) makes a map that shows spatial distribution of measurement values that have been obtained by the environment measurement.

CITATION LIST

Patent Literature

[Patent Literature 1]
Japanese Patent Application Publication Tokukai No. 2005-16931 (Publication date: Jan. 20, 2005)
[Patent Literature 2]
Japanese Patent Application Publication Tokukai No. 2008-254167 (Publication date: Oct. 23, 2008)
[Patent Literature 3]
Japanese Patent Application Publication Tokukai No. 2013-32926 (Publication date: Feb. 14, 2013)

SUMMARY OF INVENTION

Technical Problem

Also in a manufacturing environment such as a factory, a technique of visualizing spatial distribution of measurement values in a workplace is required so as to manage a working environment of a worker who moves in the workplace. However, in a case where the technique disclosed in each of Patent Literatures 1 through 3 is intended to be used, it is necessary to introduce the robot or the vehicle. This disadvantageously costs considerably. Furthermore, in a case where the robot or the vehicle is caused to move in a workplace and the like other than an exclusive path in a factory, it is technically difficult to automatically control movement of the robot or the vehicle, so that the movement of the robot or the vehicle is highly likely to become a hindrance to worker's work. Thus, causing the robot or the vehicle to move in a workplace and the like other than an exclusive path in a factory is not realistic. Therefore, according to the conventional techniques as disclosed in Patent Literatures 1 to 3, it is not possible to suitably manage a working environment of a worker who moves in a workplace.

The present invention has been made in view of the above problems, and an object of the present invention is to achieve (i) a management method for suitably managing a working environment of a worker who moves in a workplace and (ii) a technique relevant to the management method.

Solution to Problem

In order to attain the above object, a management method in accordance with an aspect of the present invention is a method for managing a working environment of a worker who moves in a workplace, including: a receiving process of receiving, from a mobile device worn by the worker, (i) a measurement value that has been obtained in a measuring process of carrying out environment measurement and (ii) positional information indicative of a location at which the measuring process has been carried out; and a making process of making, with reference to the measurement value and the positional information, a map that shows spatial distribution of measurement values in the workplace.

According to the above configuration, the mobile device worn by the worker who moves in the workplace carries out the environment measurement. With reference to the measurement value and the positional information received from the mobile device, the map that shows the spatial distribution of the measurement values in the workplace is made. Therefore, it is possible to suitably manage the working environment of the worker who moves in the workplace, as compared with a configuration in which a robot is used to carry out the environment measurement as in the technique disclosed in each of Patent Literatures 1 and 2 and a configuration in which a vehicle is used to carry out the environment measurement as in the technique disclosed in Patent Literature 3.

Advantageous Effects of Invention

According to an aspect of the present invention, it is possible to achieve (i) a management method for suitably managing a working environment of a worker who moves in a workplace and (ii) a technique relevant to the management method.

DESCRIPTION OF EMBODIMENTS

Embodiment 1

The following description will discuss Embodiment 1 of the present invention in detail.

[Management Method]

Figure 1:
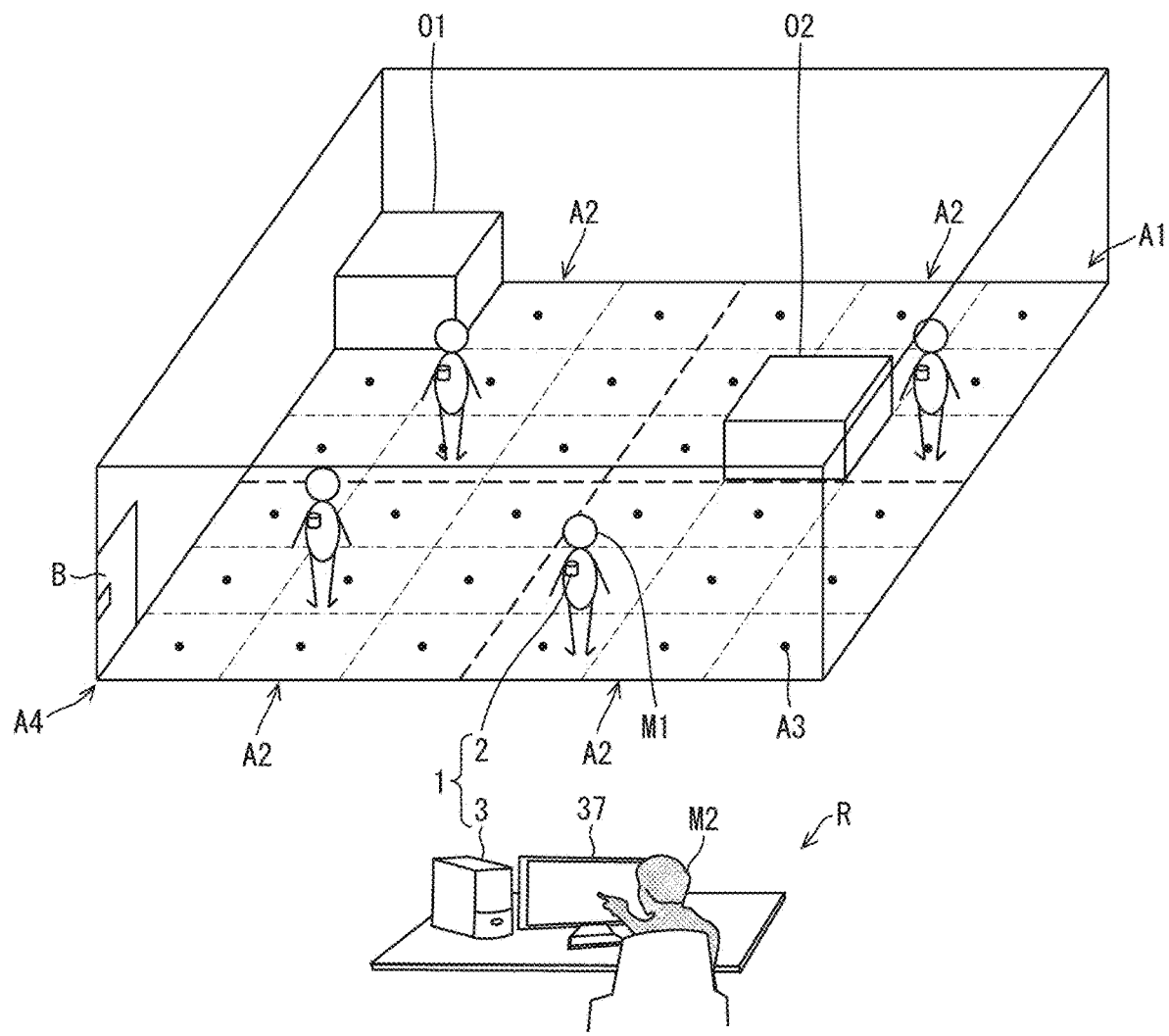
FIG. 1 is a schematic view illustrating a management method in accordance with Embodiment 1 of the present invention.

First, an outline of a management method for managing a working environment of each of workers M1 who move in a workplace A1, which method is carried out by a management system 1 in accordance with Embodiment 1, will be described below with reference to FIG. 1. As illustrated in FIG. 1, the management system 1 includes mobile devices 2 and a management device 3.

(Environment Measurement)

FIG. 1 is a schematic view for describing the management method in accordance with Embodiment 1. According to an example illustrated in FIG. 1, the workplace A1, which is a limited area such as a factory, is divided into four unit workplaces A2 each of which has 3×3 sections. Four workers M1 move in the respective unit workplaces A2 (excluding a region in which a material storage O1 is disposed and a region in which a facility O2 is disposed). The four workers M1 wear the respective mobile devices 2 on, for example, their clothes. The mobile devices 2 worn by the respective four workers M1 are moved in the respective unit workplaces A2, as the respective four workers M1 move. Each of the mobile devices 2 carries out a measuring process of carrying out environment measurement, in a corresponding one of the unit workplaces A2, with use of various sensors such as a dust sensor 21a, an acceleration sensor 21b, a light sensor 21c, a sound sensor 21d, and a temperature and humidity sensor 21e. The various sensors are attached to a main body of the each of the mobile devices 2 so that the various sensors are exposed to an environment of the workplace A1. The various sensors are connected to the each of the mobile devices 2 by wire or wireless. Note that the various sensors used to carry out the environment measurement are not limited to the above examples. The workers M1 can use any kind of sensor necessary to measure the working environment, such as an atmospheric pressure sensor (not illustrated) and a gas sensor (not illustrated).

Note, here, that a unit workplace indicates a workplace that serves as a unit based on which a mobile device worn by a worker carries out a measuring process. Note also that the unit workplace is not limited to the above example and can be any region, provided that, in a region in which work involving a hazardous substance such as free silicic acid is carried out, the unit workplace is a region in which it is considered necessary to manage the worker in consideration of (i) a range of movement of the worker while the worker is at work and (ii) distribution of a concentration of the hazardous substance. Note also that, according to the above example, the four workers M1 move in the respective unit workplaces A2, and the mobile devices 2 worn by the respective four workers M1 each carry out the environment measurement. However, in Embodiment 1, it is only necessary that at least one worker move in a workplace and a mobile device worn by the at least one worker carry out environment measurement in the workplace.

According to the example illustrated in FIG. 1, in the workplace A1, each of the unit workplaces A2 is divided into nine sections, and respective center points of the nine sections are defined as measurement points A3 which are necessary to make a map that shows spatial distribution of measurement values (in Embodiment 1, spatial distribution of a hazardous substance). When each of the four workers M1 passes through each of the measurement points A3, a corresponding one of the mobile devices 2 which one is worn by the each of the four workers M1 carries out, at the each of the measurement points (predetermined location) A3, the measuring process of carrying out the environment measurement with use of the various sensors such as the dust sensor 21a.

This allows locations at each of which the measuring process is carried out (hereinafter, referred to as measurement locations) to be less concentrated at a specific location. As a result, it is possible for the management device 3 to suitably make the map that shows the spatial distribution of the measurement values in the workplace A1. The management device 3 outputs the map thus made to an output device (display device) 37. As a result, as illustrated in FIG. 1, it is possible for a manager M2 in a management room R to suitably manage the workers M1 who move in the respective unit workplaces A2, by, for example, checking the map displayed by the output device 37. The map will be later described in detail.

Note that, according to the above example, each of the mobile devices 2 carries out the environment measurement at each of the measurement points A3 so that the measurement locations are less concentrated at a specific location. In Embodiment 1, instead of the measurement locations, intervals at which the measuring process is carried out (hereinafter, referred to as measurement intervals) can be alternatively adjusted. In this case, each of the mobile devices 2 shortens the measurement intervals, as a speed at which a corresponding one of the workers M1 moves (acceleration) becomes faster. Specifically, each of the mobile devices 2 shortens the measurement intervals, in a case where a speed at which a corresponding one of the workers M1 moves (acceleration) is fast. In contrast, each of the mobile devices 2 lengthens the measurement intervals, in a case where a speed at which a corresponding one of the workers M1 moves (acceleration) is slow (for example, in a case where the corresponding one of the workers M1 hardly moves). This also allows the measurement locations to be less concentrated at a specific location.

Note, here, that each of the mobile devices 2 is configured such that, in a case where the measuring process is carried out with use of the above dust sensor 21a, air is blown to the dust sensor 21a. More specifically, each of the mobile devices 2 is configured such that (i) air is not blown to the dust sensor 21a in normal times other than a timing at which the environment measurement (for example, the environment measurement on the hazardous substance) is carried out with use of the dust sensor 21a and (ii) air is blown to the dust sensor 21a by a fan (not illustrated) or the like merely at the timing at which the environment measurement is carried out with use of the dust sensor 21a (for example, immediately before the environment measurement is carried out with use of the dust sensor 21a).

Note, here, that, in a case where a dust sensor has a mobile size, the dust sensor generally measures a concentration of dust, such as fumes, by a dust suction method in which the dust is sucked with use of a hot draft, due to a battery issue. However, according to the dust suction method, a speed at which the dust is sucked into the dust sensor (a speed at which the dust moves) is slower than a speed at which a worker M1 moves. Therefore, there is a possibility that the concentration (measurement value) of the dust, which concentration has been obtained in a measuring process of carrying out environment measurement with use of the dust sensor, does not correspond to (match) a location at which the measuring process has been carried out. Further, in a case where the worker causes the measuring process to be carried out with use of the dust sensor while the worker is moving, there is also a possibility that the dust sensor cannot obtain a sufficient amount of atmospheric air (air). Moreover, in a case where (i) a suction device such as a fan is provided to the dust sensor and (ii) atmospheric air (air) containing the dust (floating dust) in an amount necessary for measurement is sucked into the dust sensor, a problem that an amount of consumption of a battery is increased is raised.

In contrast, according to Embodiment 1, as described above, each of the mobile devices 2 is configured such that air is blown to the dust sensor 21a merely at the timing at which the environment measurement is carried out with use of the dust sensor 21a. This makes it possible to (i) suppress an amount of consumption of a battery and (ii) decrease an amount of dirt accumulated on a surface of the dust sensor 21a.

As described above, each of the mobile devices 2 repeats the environment measurement at each of the measurement points A3 included in a corresponding one of the unit workplaces A2. Each of the mobile devices 2 thus carries out, in a corresponding one of the unit workplaces A2, the measuring process of carrying out the environment measurement. Each of the mobile devices 2 carries out the measuring process with use of the various sensors such as the dust sensor 21a.

(Identification of Location)

According to the example illustrated in FIG. 1, each of the mobile devices 2 identifies a location at which the each of the mobile devices 2 has carried out the measuring process, with reference to (i) an initial location A4 which is a location corresponding to a transmitter B of a beacon (radio beacon) attached to an entrance of the workplace A1 and which has been identified by the beacon and (ii) an acceleration which has been detected by the acceleration sensor 21b. Specifically, each of the mobile devices 2 obtains, from the transmitter B of the beacon, the initial location A4 which has been identified by the beacon. Subsequently, the each of the mobile devices 2 calculates the speed by integrating the acceleration which has been detected by the acceleration sensor 21b, and then further integrates the speed so as to calculate a distance from the initial location A4. The each of the mobile devices 2 identifies a location, for example, by calculating coordinates from the distance while regarding the initial location A4 as an origin. In this manner, use of a radio beacon, such as the transmitter B of the beacon, and the acceleration sensor 21b in combination makes it possible to identify, with high accuracy, the location at which the measuring process has been carried out, as compared with a case where the location is identified with use of merely the radio beacon or merely the acceleration sensor. Moreover, it is possible to identify the location without use of numerous radio beacons. This allows a decrease in cost.

(Transmission and Reception of Measurement Value and Positional Information)

Each of the mobile devices 2 transmits, to the management device 3, (i) a measurement value that has been obtained in the measuring process of carrying out the environment measurement and (ii) positional information indicative of the location that has been identified in a location identifying process of identifying the location at which the measuring process has been carried out, in association with each other. The management device 3 receives the measurement value and the positional information from the each of the mobile devices 2.

(Making of Map that Shows Spatial Distribution of Measurement Values in Workplace A1)

The management device 3 makes the map that shows the spatial distribution of the measurement values in the workplace A1, with reference to the measurement value and the positional information which have been received from each of the mobile devices 2.

According to the above configuration, the mobile devices 2 are worn by the respective four workers M1 who move in the respective unit workplaces A2. Each of the mobile devices 2 carries out the environment measurement. The management device 3 makes the map that shows the spatial distribution of the measurement values in the unit workplaces A2, with reference to the measurement value and the positional information which have been received from each of the mobile devices 2. Therefore, it is possible to suitably manage a working environment of a worker who moves in a workplace, as compared with a configuration in which a robot is used to carry out environment measurement as in the technique disclosed in each of Patent Literatures 1 and 2 and a configuration in which a vehicle is used to carry out environment measurement as in the technique disclosed in Patent Literature 3. As a result, it is possible for the manager M2 to suitably manage the workers M1 who move in the respective four unit workplaces A2 by, for example, checking the map displayed by the output device (display device) 37. Furthermore, it is possible for the manager M2 to intuitively understand a condition of the workplace A1, which is a large region including the unit workplaces A2, by checking the map displayed by the output device 37. This promotes "visualization" of the workplace A1, and consequently allows the workplace A1 to be a place where the workers M1 can move without anxiety. Moreover, it is possible for the manager M2 to (i) promptly find a deterioration of an environmental condition in each of the unit workplaces A2 in which the respective workers M1 move and (ii) prevent the environmental condition from being deteriorated, by, for example, analyzing the measurement values and accordingly controlling or maintaining facilities and the like. Besides, according to the above management method, it is only necessary that the workers M1 who wear the respective mobile devices 2 move and the manager M2 check the map made by the management device 3. Therefore, it is possible to manage, at a low cost, the working environment of each of the workers M1 who move in the respective unit workplaces A2.

Every time the management device 3 receives, from each of the mobile devices 2, (i) the measurement value that has been newly obtained by the environment measurement and (ii) the positional information indicative of the location at which the measuring process has been newly carried out, the management device 3 makes the map in which one of the measurement values which one corresponds to, in the map, the location at which the measuring process has been newly carried out is replaced with the measurement value that has been newly obtained in the measuring process. This makes it possible to suitably make the map that shows the spatial distribution of the latest measurement values in the workplace A1. As a result, it is possible for the manager M2 to more suitably manage the working environment of each of the workers M1 who move in the workplace A1.

(Identification of Management Class)

After the management device 3 makes the map that shows the spatial distribution of the measurement values in the workplace A1, the management device 3 can identify a management class of each of the unit workplaces A2. Specifically, the management device 3 identifies the management class of each of the unit workplaces A2 by comparing (i) an average or a maximum value of the measurement values that have been obtained by the environment measurement on the hazardous substance in the each of the unit workplaces A2 with (ii) a management concentration which is a predetermined concentration corresponding to the hazardous substance (for example, free silicic acid). The management concentration E (mg/m$^3$) which is a predetermined concentration is calculated as in the following Expression (1) with use of a free silicic acid content Q (%) of dust which free silicic acid content is inputted in each of the mobile devices 2 in advance. Note that, for example, it is possible for the management device 3 to calculate the average and the maximum value of the measurement values with reference to the measurement values that have been obtained during predetermined time. The management class will be later described in detail.

$$E=3.0/(1.19Q+1) \tag{1}$$

As described above, it is possible to suitably identify the management class of each of the unit workplaces A2 by comparing an average or a maximum value of a concentration of the dust with the management concentration which is a predetermined concentration corresponding to free silicic acid, without an expert carrying out the environment measurement on the hazardous substance and analyzing data. This makes it possible for the manager M2 to more suitably manage the working environment of each of the workers M1 who move in the respective unit workplaces A2 which contain the hazardous substance such as free silicic acid.

After the management device 3 identifies the management class, the management device 3 makes the map that discernibly shows the management class of each of the unit workplaces A2 included in the workplace A1, by superimposing the management class on the map that shows the spatial distribution of the measurement values in the workplace A1.

(Display of Map that Shows Spatial Distribution of Measurement Values in Workplace A1)

The management device 3 outputs, to the output device (display device) 37, the map that has been thus made and that shows the spatial distribution of the measurement values in the workplace A1, and causes the output device 37 to display the map. In a case where the management device 3 does not identify the management class, the management device 3 causes the output device 37 to display the map on which the management class is not superimposed. In a case where the management device 3 has identified the management class, the management device 3 causes the output device 37 to display the map on which the management class is superimposed.

[Configuration of Mobile Device 2]

Figure 2:
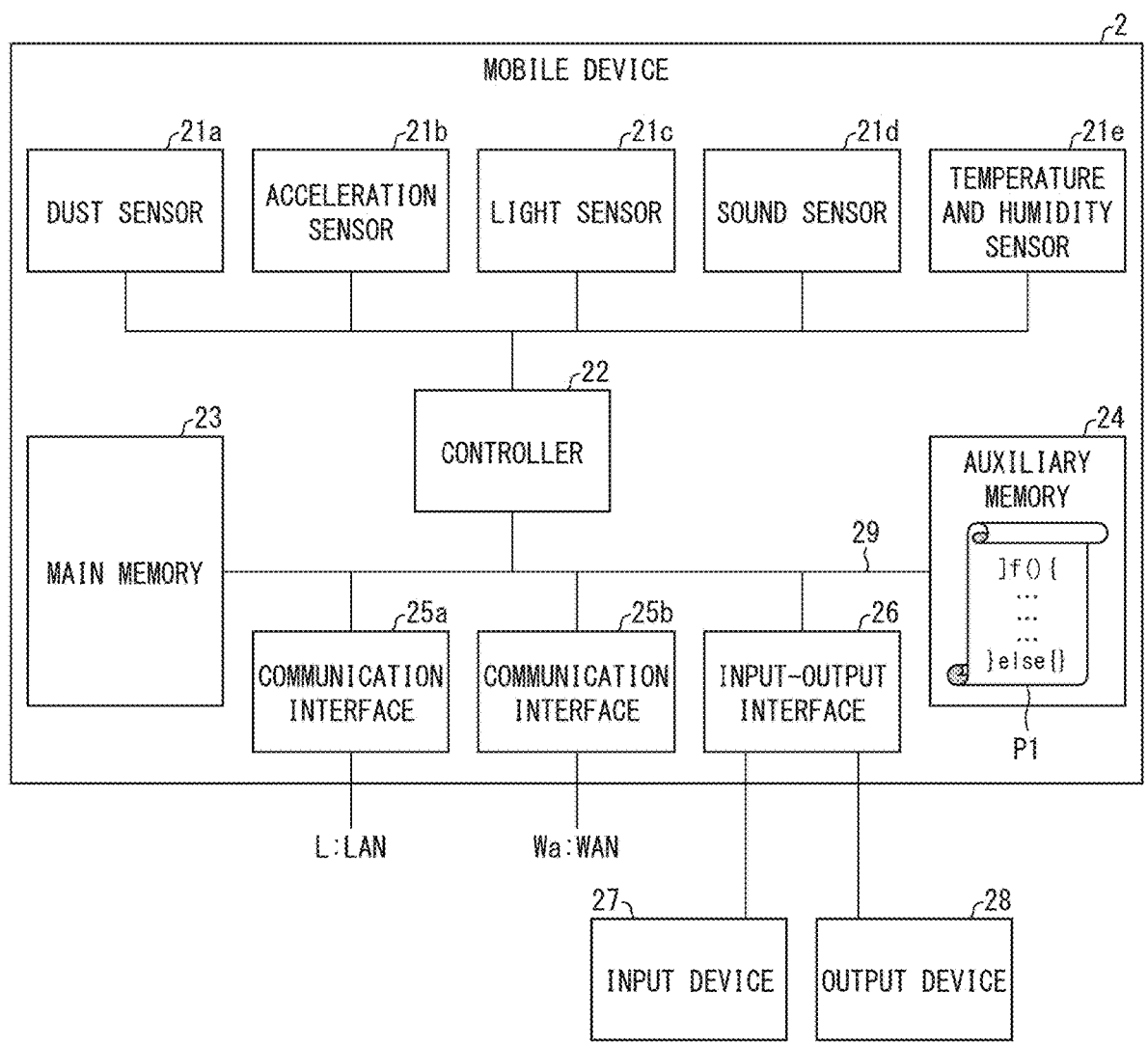
FIG. 2 is a block diagram illustrating a configuration of a mobile device in accordance with Embodiment 1 of the present invention.

Next, a configuration of each of the mobile devices 2 in accordance with Embodiment 1 will be described with reference to FIG. 2. FIG. 2 is a block diagram illustrating a configuration of a mobile device 2 in accordance with Embodiment 1.

As illustrated in FIG. 2, the mobile device 2 is a computer including the dust sensor 21a, the acceleration sensor 21b, the light sensor 21c, the sound sensor 21d, the temperature and humidity sensor 21e, a controller 22, a main memory 23, an auxiliary memory 24, a communication interface 25a, a communication interface 25b, and an input-output interface 26. The dust sensor 21a, the acceleration sensor 21b, the light sensor 21c, the sound sensor 21d, the temperature and humidity sensor 21e, the controller 22, the main memory 23, the auxiliary memory 24, the communication interface 25a, the communication interface 25b, and the input-output interface 26 are connected to each other via a bus 29. As the controller 22, for example, a single or a plurality of microprocessors, a single or a plurality of digital signal processors, a single or a plurality of microcontrollers, or a combination thereof can be used. As the main memory 23, for example, a single or a plurality of semiconductor random access memories (RAMs) can be used. As the auxiliary memory 24, for example, a single or a plurality of hard disk drives (HDDs), a single or a plurality of solid state drives (SSDs), or a combination of thereof can be used. Part or all of the auxiliary memory 24 can be a storage on a network which storage is connected via the communication interface 25b. The communication interface 25a is connected to the transmitter B of the beacon via a wireless LAN L. The communication interface 25b is connected to the management device 3 via a WAN Wa such as the Internet. As the input-output interface 26, for example, a universal serial bus (USB) interface, a near field communication interface such as an infrared interface and Bluetooth (registered trademark), or a combination thereof can be used.

To the input-output interface 26, an input device 27 and the output device 28 are, for example, connected. As the input device 27, for example, a keyboard, a mouse, a touch pad, a microphone, or a combination thereof can be used. As the output device 28, for example, a display, a printer, a speaker, or a combination thereof can be used. Note that a keyboard and a touch pad each of which functions as the input device 27 and a display which functions as the output device 28 can be embedded in the mobile device 2 like a notebook computer. Note also that a touch panel which functions as the input device 27 and the output device 28 can be embedded in the mobile device 2 like a smartphone or a tablet computer.

In the auxiliary memory 24, a program P1 is stored. The program P1 is a program for causing the controller 22 to carry out processes in steps S101 through S107 (later described). The controller 22 loads, on the main memory 23, the program P1 stored in the auxiliary memory 24, and executes each command which is contained in the program P1 loaded on the main memory 23. The controller 22 thereby carries out each step included in each of the processes in the steps S101 through S107 (later described). Further, in the auxiliary memory 24, various pieces of data to which the controller 22 refers so as to carry out the processes in the steps S101 through S107 (later described) are stored.

Note, according to the above example, the dust sensor 21a, the acceleration sensor 21b, the light sensor 21c, the sound sensor 21d, and the temperature and humidity sensor 21e are connected to the controller 22 by wire, that is, via the bus 29. Note, however, that, in Embodiment 1, the dust sensor 21a, the acceleration sensor 21b, the light sensor 21c, the sound sensor 21d, and the temperature and humidity sensor 21e can be alternatively connected to the controller 22 by wireless.

Note also that the above example has discussed a mode in which the controller 22 carries out the processes in the steps S101 through S107 (later described) in accordance with the program P1 stored in the auxiliary memory 24 which is an internal storage medium. However, a mode can be alternatively employed in which the controller 22 carries out the processes in the steps S101 through S107 (later described) in accordance with the program P1 stored in an external storage medium. In this case, the external storage medium can be a computer-readable "non-transitory tangible medium" such as a tape, a disk, a card, a semiconductor memory, or a programmable logic circuit. Alternatively, a mode can be employed in which the controller 22 carries out the processes in the steps S101 through S107 (later described) in accordance with the program P1 obtained on the network connected via the communication interface 25b. In this case, the network can be, for example, the Internet, a wired local area network (LAN), a wireless LAN, or a combination of at least part of these networks.

[Flow of Management Process Carried Out by Mobile Device 2]

Figure 3:
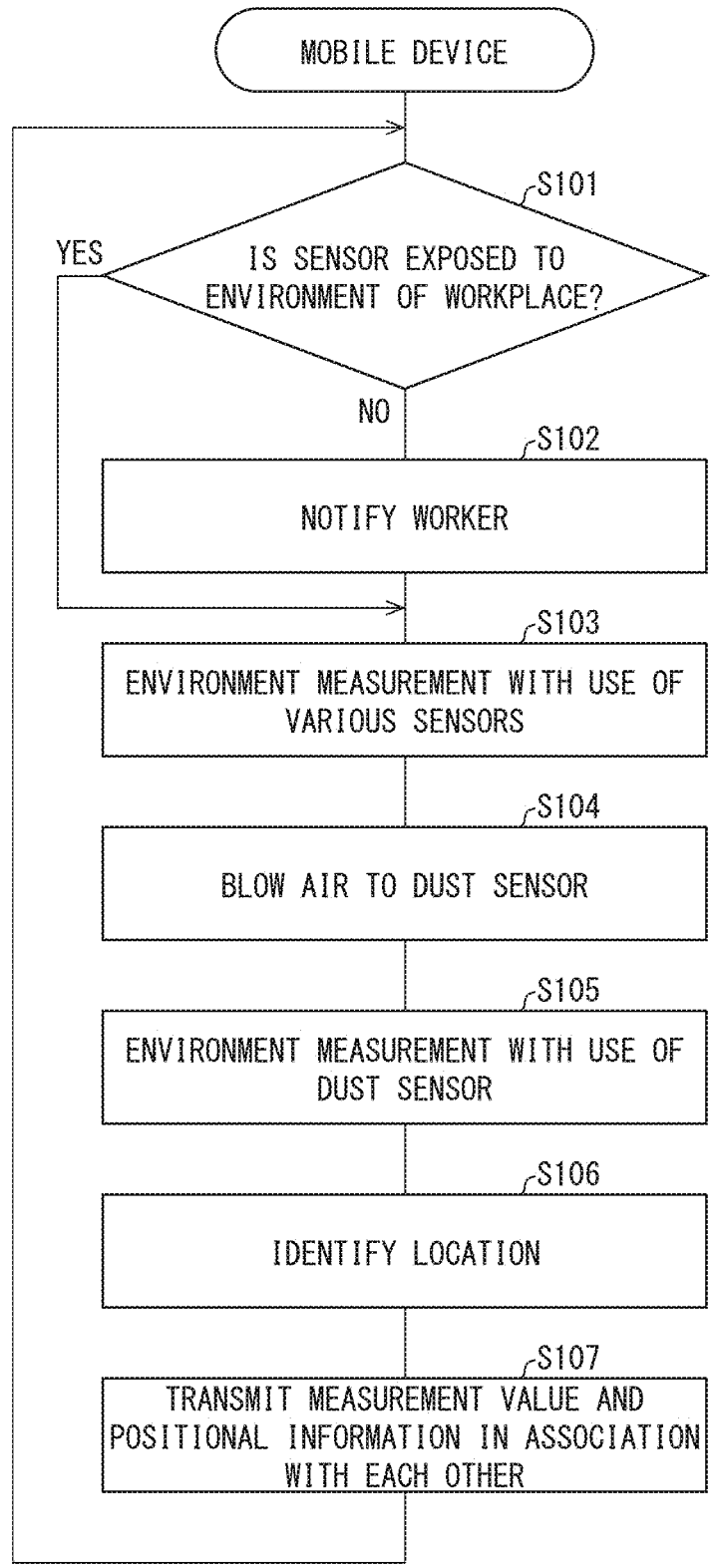
FIG. 3 is a flowchart illustrating an example of a flow of a management process carried out by the mobile device in accordance with Embodiment 1 of the present invention.

A flow of a management process carried out by the mobile device 2 configured as described above will be described with reference to FIG. 3. FIG. 3 is a flowchart illustrating an example of a flow of the management process carried out by the mobile device 2 in accordance with Embodiment 1.

In the step S101, the controller 22 of the mobile device 2 determines whether or not at least the dust sensor 21a, out of the various sensors, is exposed to the environment of the workplace A1. In other words, the controller 22 of the mobile device 2 determines whether or not the dust sensor 21a is placed at a location at which the dust sensor 21a is in contact with atmospheric air (external air) in the workplace A1. In a case where the controller 22 of the mobile device 2 determines that the dust sensor 21a is exposed to the environment of the workplace A1, the management process proceeds to the step S103. In a case where the controller 22 of the mobile device 2 determines that the dust sensor 21a is not exposed to the environment of the workplace A1, the management process proceeds to the step S102.

In the step S102, in a case where the controller 22 of the mobile device 2 determines that the dust sensor 21a is not exposed to the environment of the workplace A1, the controller 22 controls a notification to be sent to a worker M1 (notifying process). As an example, in a case where (i) the light sensor (illuminance sensor) 21c is provided near the dust sensor 21a and (ii) the dust sensor 21a is not attached to a location near the face of the worker M1 (such as a helmet of the worker M1 or a chest part or a shoulder part of working clothes of the worker M1) by a fixing member, the light sensor 21c raises an alarm. In a case where the various sensors, such as the dust sensor 21a, which are used to carry out the measuring process are not worn by the worker M1 under a normal condition, errors occur in measurement values obtained by the environment measurement. However, by notifying the worker M1 as described above, it is possible to prevent errors from occurring.

In the step S103, the controller 22 of the mobile device 2 controls the environment measurement to be carried out with use of the sensors, such as the light sensor 21c, the sound sensor 21d, and the temperature and humidity sensor 21e.

In the step S104, the controller 22 of the mobile device 2 controls air to be blown out to the dust sensor 21a by a fan (not illustrated) or the like before (for example, immediately before) the measuring process is carried out (air blowing process).

In the step S105, the controller 22 of the mobile device 2 controls the environment measurement to be carried out with use of the sensors, such as the dust sensor 21a, worn by the worker M1 (measuring process). As an example, the mobile device 2 carries out the measuring process by carrying out the environment measurement on the hazardous substance, such as free silicic acid, at predetermined locations, such as the measurement points A3, in the workplace A1. Further, as an example, the mobile device 2 shortens the measurement intervals, as a speed at which the worker M1 moves becomes faster.

In the step S106, the controller 22 of the mobile device 2 identifies the location at which the measuring process of carrying out the environment measurement has been carried out (location identifying process). As an example, the mobile devices 2 obtains, from the transmitter B of the beacon via the communication interface 25a, the initial location A4 which is a location corresponding to the transmitter B of the beacon (radio beacon) attached to the entrance of the workplace A1 and which has been identified by the beacon. Further, the mobile device 2 identifies the location with reference to the initial location A4 and the acceleration detected by the acceleration sensor 21b.

In the step S107, the controller 22 of the mobile device 2 transmits, to the management device 3 via the communication interface 25b, (i) the measurement value that has been obtained in the measuring process and (ii) the positional information indicative of the location that has been identified in the location identifying process, in association with each other (transmitting process). After the step S107, the controller 22 of the mobile device 2 repeats the above-described processes from the step S101.

Note that, according to the above example, the controller 22 of the mobile device 2 determines, in the step S101, whether or not at least the dust sensor 21a, out of the various sensors, is exposed to the environment of the workplace A1. Note also that, in the step S102, in a case where the controller 22 of the mobile device 2 determines that the dust sensor 21a is not exposed to the environment of the workplace A1, the controller 22 controls the notification to be sent to the worker M1. Note, however, that, in Embodiment 1, the controller 22 of the mobile device 2 can alternatively control the notification to be sent to the worker M1, in a case where the sensors, such as the dust sensor 21a, are not attached to the main body of the mobile device 2 so that the sensors are exposed to the workplace A1 or in a case where the sensors are not connected to the mobile device 2 by wire or wireless.

Note also that, according to the above example, in the step S105, the controller 22 of the mobile device 2 controls the environment measurement to be carried out on, for example, the hazardous substance with use of the sensors, such as the dust sensor 21a, worn by the worker M1. In Embodiment 1, the controller 22 of the mobile device 2 can alternatively control the environment measurement to be carried out on, for example, a temperature with use of the temperature and humidity sensor 21e worn by the worker M1, instead of the environment measurement on the hazardous substance. In this case, the controller 22 of the mobile device 2 can omit the processes in the steps S104 and S105, and can carry out merely the processes in the steps S101 through S103, S106, and S107. This also allows a controller 31 of the management device 3 to make a map that shows spatial distribution of measurement values of the temperature or the like, with reference to a measurement value of the temperature or the like received from the mobile device 2. As a result, it is possible to suitably manage the working environment of the worker M1 who moves in the workplace A1.

[Configuration of Management Device 3]

Figure 4:
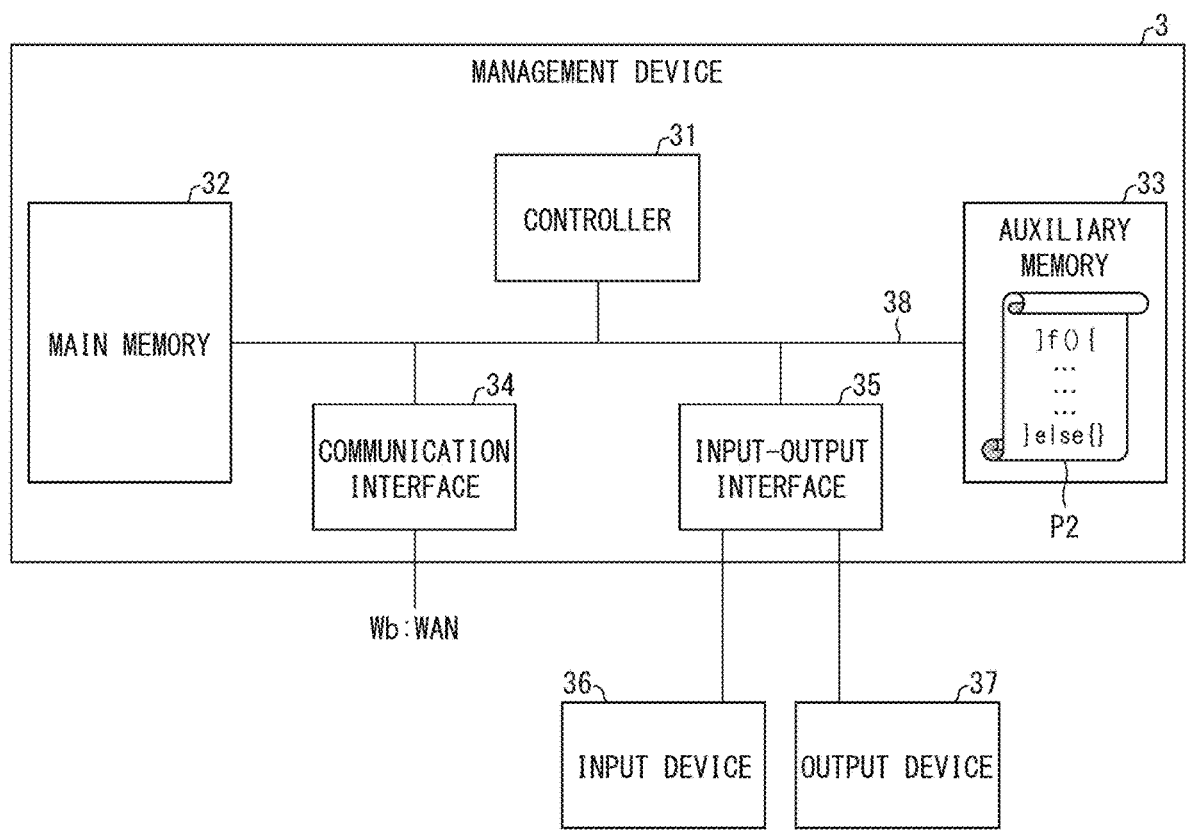
FIG. 4 is a block diagram illustrating a configuration of a management device in accordance with Embodiment 1 of the present invention.

Next, a configuration of the management device 3 in accordance with Embodiment 1 will be described with reference to FIG. 4. FIG. 4 is a block diagram illustrating the configuration of the management device 3 in accordance with Embodiment 1.

As illustrated in FIG. 4, the management device 3 is a computer including the controller 31, a main memory 32, an auxiliary memory 33, a communication interface 34, and an input-output interface 35. The controller 31, the main memory 32, the auxiliary memory 33, the communication interface 34, and the input-output interface 35 are connected to each other via a bus 38. As the controller 31, for example, a single or a plurality of microprocessors, a single or a plurality of digital signal processors, a single or a plurality of microcontrollers, or a combination thereof can be used. As the main memory 32, for example, a single or a plurality of semiconductor random access memories (RAMs) can be used. As the auxiliary memory 33, for example, a single or a plurality of hard disk drives (HDDs), a single or a plurality of solid state drives (SSDs), or a combination of thereof can be used. Part or all of the auxiliary memory 33 can be a storage on a network which storage is connected via the communication interface 34. The communication interface 34 is connected to each of the mobile devices 2 via a WAN Wb such as the Internet. As the input-output interface 35, for example, a universal serial bus (USB) interface, a near field communication interface such as an infrared interface and Bluetooth (registered trademark), or a combination thereof can be used.

To the input-output interface 35, an input device 36 and the output device 37 are, for example, connected. As the input device 36, for example, a keyboard, a mouse, a touch pad, a microphone, or a combination thereof can be used. As the output device 37, for example, a display, a printer, a speaker, or a combination thereof can be used. According to the example illustrated in FIG. 1, the output device 37 is a display device including a display. Note that a keyboard and a touch pad each of which functions as the input device 36 and a display which functions as the output device 37 can be embedded in the management device 3 like a notebook computer. Note also that a touch panel which functions as the input device 36 and the output device 37 can be embedded in the management device 3 like a smartphone or a tablet computer.

In the auxiliary memory 33, a program P2 is stored. The program P2 is a program for causing the controller 31 to carry out processes in steps S201 through S205 (later described). The controller 31 loads, on the main memory 32, the program P2 stored in the auxiliary memory 33, and executes each command which is contained in the program P2 loaded on the main memory 32. The controller 31 thereby carries out each step included in each of the processes in the steps S201 through S205 (later described). Further, in the auxiliary memory 33, various pieces of data to which the controller 31 refers so as to carry out the processes in the steps S201 through S205 (later described) are stored.

Note here that a mode has been described in which the controller 31 carries out the processes in the steps S201 through S205 (later described) in accordance with the program P2 stored in the auxiliary memory 33 which is an internal storage medium. However, the management device 3 is not limited such a configuration. That is, a mode can be alternatively employed in which the controller 31 carries out the processes in the steps S201 through S205 (later described) in accordance with the program P2 stored in an external storage medium. In this case, the external storage medium can be a computer-readable "non-transitory tangible medium" such as a tape, a disk, a card, a semiconductor memory, or a programmable logic circuit. Alternatively, a mode can be employed in which the controller 31 carries out the processes in the steps S201 through S205 (later described) in accordance with the program P2 obtained on the network connected via the communication interface 34. In this case, the network can be, for example, the Internet, a wired local area network (LAN), a wireless LAN, or a combination of at least part of these networks.

[Flow of Management Process Carried Out by Management Device 3]

Figure 5:
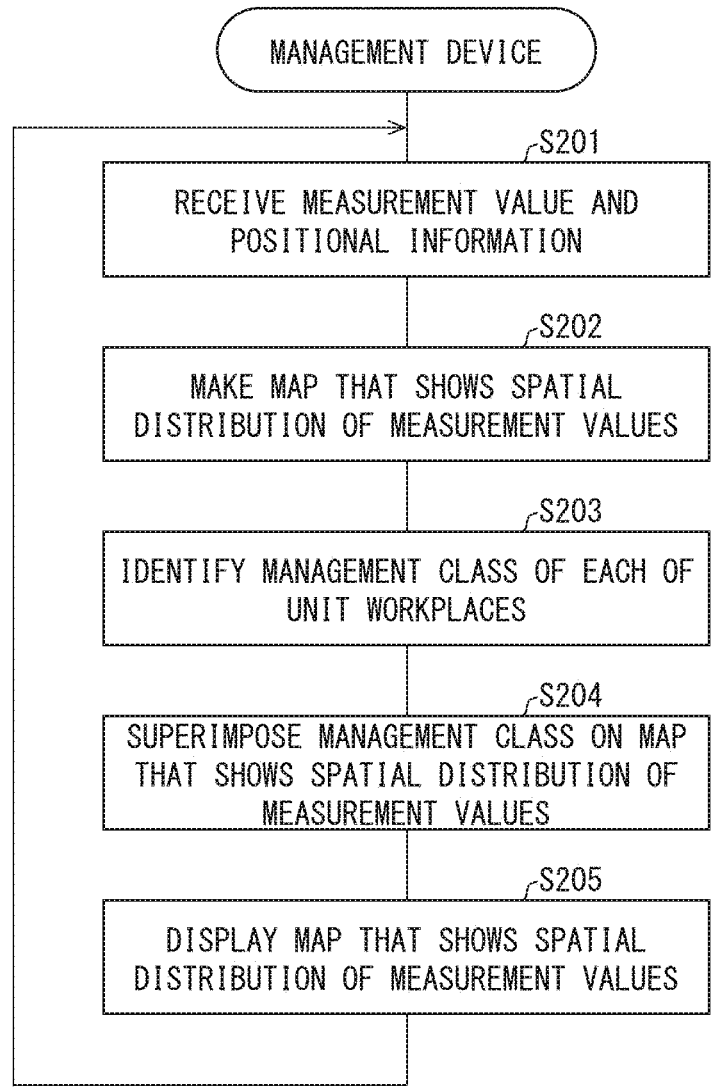
FIG. 5 is a flowchart illustrating an example of a flow of a management process carried out by the management device in accordance with Embodiment 1 of the present invention.

A flow of a management process (management method) carried out by the management device 3 configured as described above will be described with reference to FIG. 5. FIG. 5 is a flowchart illustrating an example of a flow of the management process carried out by the management device 3 in accordance with Embodiment 1.

In the step S201, the controller 31 of the management device 3 receives, from each of the mobile devices 2 worn by respective workers M1, (i) the measurement value that has been obtained in the measuring process of carrying out the environment measurement and (ii) the positional information indicative of the location at which the measuring process has been carried out, via the communication interface 34 (receiving process).

In the step S202, the controller 31 of the management device 3 makes the map that shows the spatial distribution of the measurement values in the workplace A1, with reference to the measurement value and the positional information which have been received in the step S201 (making process). As an example, the controller 31 of the management device 3 makes the map that shows the spatial distribution of the hazardous substance in the workplace A1. Note, here, that the controller 31 of the management device 3 makes the map on which the management class is not superimposed.

In the step S203, the controller 31 of the management device 3 identifies the management class of each of the unit workplaces A2 (management class identifying process). As an example, the controller 31 of the management device 3 compares (i) the average or the maximum value of the measurement values that have been obtained by the environment measurement (the concentration of the dust which concentration has been measured by the dust sensor 21a) in each of the unit workplaces A2 with (ii) the management concentration which is a predetermined concentration corresponding to the hazardous substance such as free silicic acid. The controller 31 of the management device 3 thus identifies the management class of each of the unit workplaces A2.

In the step S204, the controller 31 of the management device 3 superimposes, on the map that has been made in the step S202 and that shows the spatial distribution of the measurement values in the workplace A1, the management class of each of the unit workplaces A2 which management class has been identified in the step S203. The controller 31 of the management device 3 thus makes the map which discernibly shows the management class of each of the unit workplaces A2 included in the workplace A1 (making process).

In the step S205, the controller 31 of the management device 3 controls, via the input-output interface 35, the output device 37 to display the map thus made.

After the step S205, the controller 31 of the management device 3 repeats the above-described processes from the step S201. Every time, in the step S201, the controller 31 of the management device 3 receives, from each of the mobile devices 2, (i) the measurement value that has been newly obtained in the measuring process and (ii) the positional information indicative of the location at which the measuring process has been newly carried out, the controller 31 of the management device 3 makes, in the step S202, the map that shows the spatial distribution of the latest measurement values in the workplace A1, by replacing, with the measurement value that has been newly obtained in the measuring process, one of the measurement values which one corresponds to the location at which the measuring process has been newly carried out.

Note that, according to the above example, the controller 31 of the management device 3 carries out all the processes in the steps S201 through S205. In Embodiment 1, in a case where the controller 31 of the management device 3 repeats the above processes from the step S201 (that is, the processes loop), the controller 31 of the management device 3 can carry out the step S203 merely in a specific loop (hereinafter, also referred to as a "management class identifying loop") and omit the step S203 in a loop other than the management class identifying loop. Note, here, that a frequency at which the step S203 is carried out, that is, a proportion of the number of management class identifying loops with respect to the total number of loops is, for example, one several tenths of the total number of loops.

This makes it possible for the manager M2 to efficiently and suitably manage the working environment of each of the workers M1 who move in the workplace A1. Note that, in the step S204 in the loop other than the management class identifying loop, the controller 31 of the management device 3 superimposes, on the map that shows the spatial distribution of the measurement values, the management class that has been identified in the step S203 carried out in the last management class identifying loop. Note also that, in the step S205 in the loop other than the management class specific loop, the controller 31 of the management device 3 controls the output device 37 to display the map on which the management class that has been identified in the step S203 carried out in the last management class specific loop is superimposed. In this case, the controller 31 of the management device 3 can regard the first loop as the management class identifying loop, and carry out the process in the step S203. This makes it possible to display the map on which the management class is always superimposed.

Note also that, according to the above example, the controller 31 of the management device 3 makes, in the step S202, the map that shows the spatial distribution of the hazardous substance, as the map that shows the spatial distribution of the measurement values. In Embodiment 1, for example, the controller 31 of the management device 3 can alternatively make, in the step S202, the map that shows the spatial distribution of the measurement values of the temperature or the like, instead of the map that shows the spatial distribution of the hazardous substance. In this case, the controller 31 of the management device 3 can omit the processes in the steps S203 and S204, and can carry out merely the processes in the steps S201, S202, and S205. This also allows the controller 31 of the management device 3 to make the map that shows the spatial distribution of the measurement values of the temperature. As a result, it is possible to suitably manage the working environment of each of the workers M1 who move in the workplace A1.

[Map that Shows Spatial Distribution of Measurement Values in Workplace]

Next, an example of the map that shows the spatial distribution of the measurement values in the workplace, which map is made in Embodiment 1, will be described with reference to FIGS. 6 through 9.

(Example Display 1 of Map that Shows Spatial Distribution of Measurement Values in Workplace)

Figure 6:
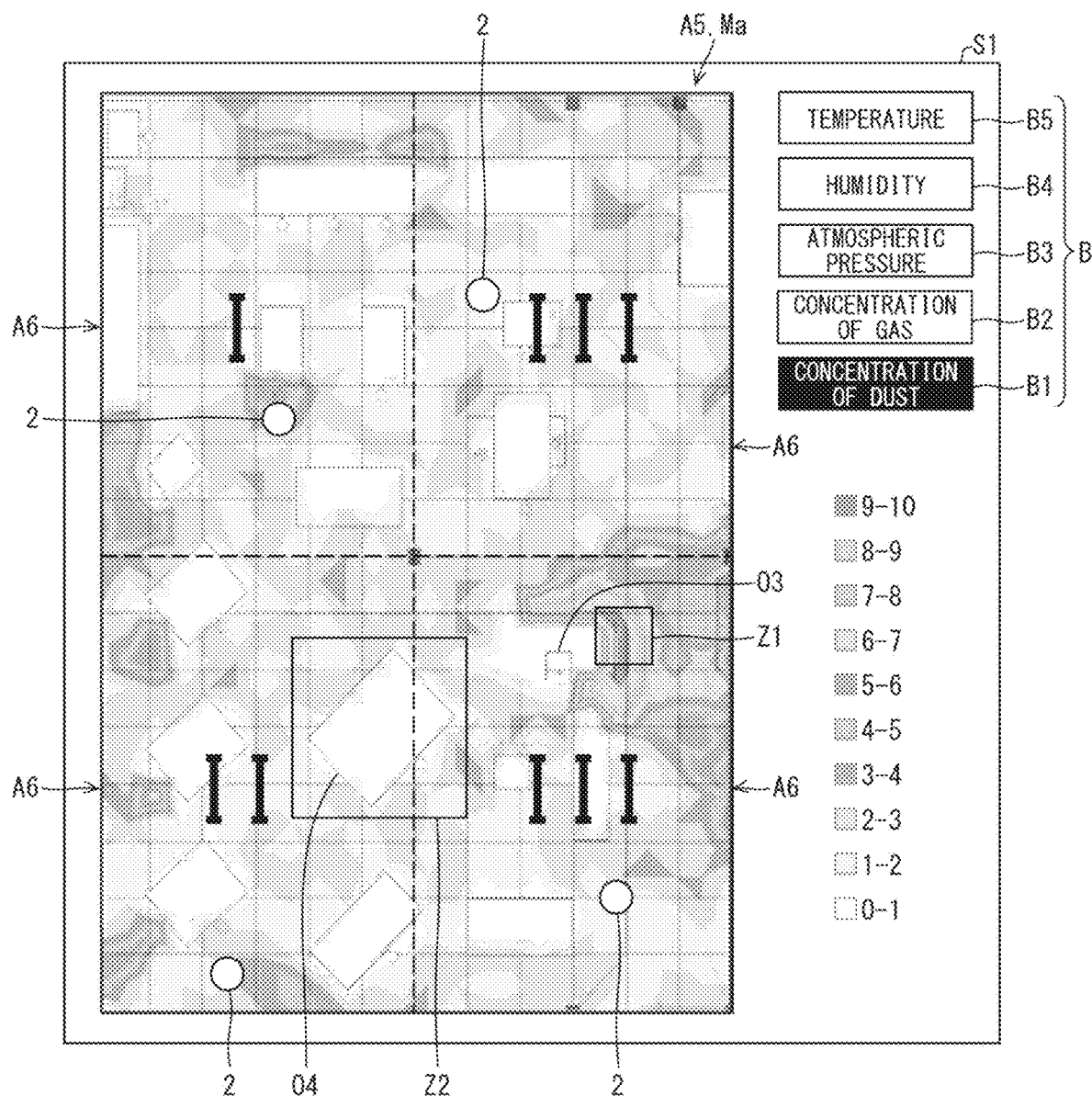
FIG. 6 is a drawing illustrating an example of a screen on which a map that is made in Embodiment 1 of the present invention and that shows spatial distribution of measurement values in a workplace is displayed.
Figure 7:
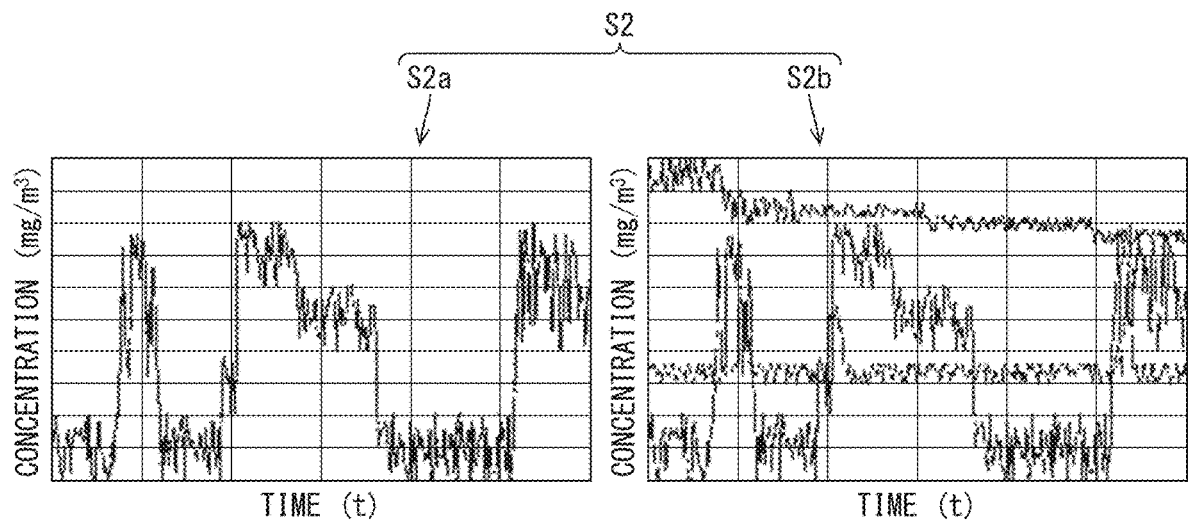
FIG. 7 is a drawing illustrating an example of a graph that is made in Embodiment 1 of the present invention and that shows temporal changes in concentration in a selective region on the map.
Figure 8:
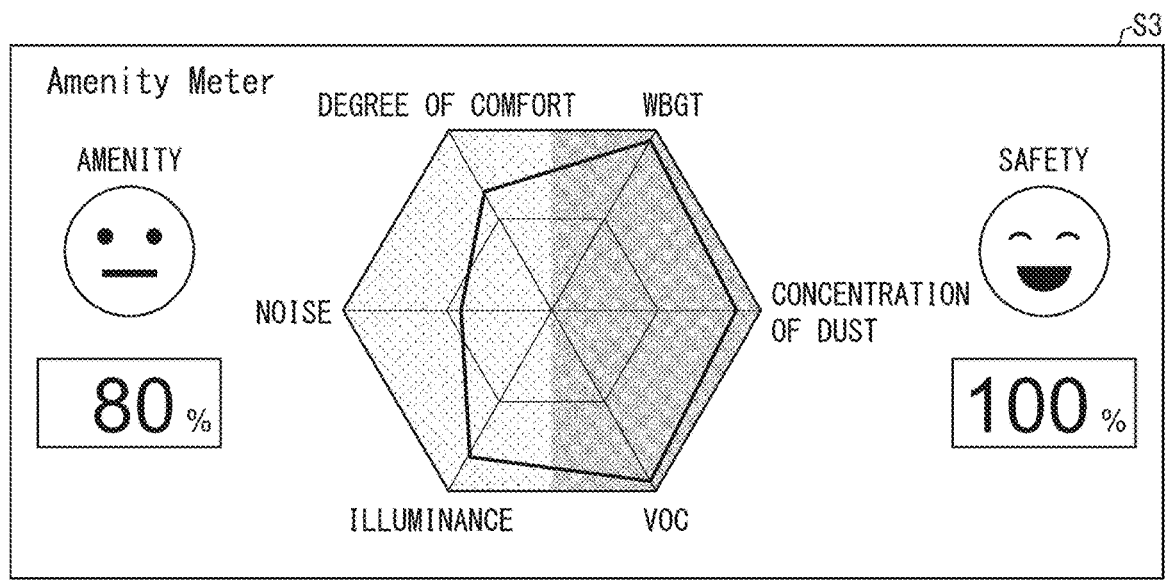
FIG. 8 is a drawing illustrating an example of an amenity meter that is made in Embodiment 1 of the present invention and that shows safety and amenity in a selective region on the map.

First, example display 1 of the map that shows the spatial distribution of the measurement values in the workplace will be described with reference to FIGS. 6 through 8. FIG. 6 is a drawing illustrating an example of a screen (first screen S1) on which a map Ma that is made in Embodiment 1 of the present invention and that shows spatial distribution of measurement values (spatial distribution of a hazardous substance) in a workplace A5 is displayed. FIG. 7 is a drawing illustrating an example of a graph that is made in Embodiment 1 and that shows temporal changes in concentration in a selective region Z1 on the map Ma. FIG. 8 is a drawing illustrating an example of an amenity meter that is made in Embodiment 1 and that shows safety and amenity in a selective region Z2 on the map Ma.

According to the map Ma illustrated in FIG. 6, out of buttons B which are constituted by buttons B1 through B5, the button B1 which is related to a concentration of dust is selected, and the concentration of the dust is displayed so that the concentration of the dust is recognized in multiple stages. A concentration of the hazardous substance, such as free silicic acid, contained in the dust is proportional to the concentration of the dust. Therefore, the map Ma shows the spatial distribution of the hazardous substance in the workplace A5 by displaying the concentration of the dust. This makes it possible to intuitively understand a condition of the workplace A5 which is a large region including unit workplaces A6. Furthermore, the map Ma shows mobile devices 2, a material storage O3, and facilities O4. Since the mobile devices 2 are thus displayed on the map Ma, it is possible for a manager M2 to suitably manage workers M1 who wear the respective mobile devices 2. Note that it is possible for the manager M2 to select any one of the buttons B1 through B5 (see FIG. 6) via an input device 36. Note that, according to the above example, the buttons B1 through B5 are displayed on the first screen S1, and it is possible for the manager M2 to switch screens by selecting any one of the buttons B1 through B4 instead of the button B5. In Embodiment 1, the first screen S1 can be alternatively configured such that tabs are displayed on the first screen S1 instead of the buttons B1 through B5 and screens are switched depending on a selected one of the tabs.

Note that, on the map Ma, a first management class I, a second management class II, or a third management class III is discernibly displayed with respect to each of the unit workplaces A6 included in the workplace A5 (see FIG. 6). Note, here, that the first management class I indicates that a risk of exceeding a management concentration (an average of the concentration of the dust) is lower than 5% or a maximum value of the concentration of the dust in a vicinity of a source from which the dust is discharged (for example, material storage O3) is lower than the management concentration. The second management class II indicates that the average of the concentration of the dust is equal to or lower than the management concentration or the maximum value of the concentration of the dust in the vicinity of the source from which the dust is discharged is not more than 1.5 times the management concentration. The third management class III indicates that the average of the concentration of the dust is higher than the management concentration or the maximum value of the concentration of the dust in the vicinity of the source from which the dust is discharged is more than 1.5 times the management concentration.

It is possible for the manager M2 to suitably manage the workers M1 who move in the workplace A5, by checking the first management class I, the second management class II, or the third management class III of each of the unit workplaces A6, which classes are discernibly displayed on the map Ma.

As an example, in a case where the first management class I is displayed on the map Ma, the manager M2 attempts to continuously maintain a current management condition of a worker M1. In a case where the second management class II is displayed on the map Ma, the manager M2 carries out an inspection on at least one of the material storage O3, the facilities (equipment) O4, and the management method. On the basis of a result of the inspection, the manager M2 attempts to take measures necessary to improve a working environment. In a case where the third management class III is displayed on the map Ma, the manager M2 carries out an inspection on at least one of the material storage O3, the facilities (equipment) O4, and the management method. On the basis of a result of the inspection, the manager M2 attempts to take measures necessary to improve the working environment. Moreover, the manager M2 makes the worker M1 use effective respiratory protective equipment. Furthermore, the manager M2 (i) makes the worker M1 receive a medical check-up and (ii) takes measures necessary to make the worker M1 stay healthy, in a case where an industrial physician considers it necessary for the manager M2 to do so. In addition, after the manager M2 takes measures to improve the working environment, the manager M2 makes the worker M1 carry out working environment measurement again, and checks whether or not the third management class III turns to the first management class I or the second management class II.

Note, here, that a lower right unit workplace A6 on the map Ma has the third management class III. Note also that the concentration of the dust in the selective region Z1 near the material storage O3 in the lower right unit workplace A6 is particularly high, and an environmental condition is worse. In this case, as has been described, the manager M2 can select, via the input device 36, the selective region Z1 near the material storage O3 in the lower right unit workplace A6 on the map Ma displayed by an output device 37.

Each selective region, such as the selective regions Z1 and Z2, on the map Ma functions as a UI element for causing a transition from the first screen S1, on which the map Ma is displayed, to a second screen S2 on which the graph that shows the temporal changes in concentration of the dust and the like (see FIG. 7) is displayed or a third screen S3 on which the amenity meter that shows the safety and the amenity (see FIG. 8) is displayed. Therefore, in a case where the manager M2 selects the selective region Z1 so that the second screen S2 is displayed, a transition to the second screen S2 occurs. On a second screen S2a on a left side of FIG. 7, a graph that shows temporal changes in concentration of the dust in the selective region Z1 on the map Ma is displayed. On a second screen S2b on a right side of FIG. 7, a graph that shows temporal changes in concentration of the dust, temperature, and humidity in the selective region Z1 on the map Ma is displayed. It is possible for the manager M2 to recognize the concentration of the dust in the selective region Z1, which is a narrow region, on the second screen S2a. It is possible for the manager M2 to easily recognize a correlation between the concentration of the dust, the temperature, and the humidity by causing the temperature and the humidity to be displayed in addition to the concentration of the dust as in the second screen S2b. As a result, it is possible for the manager M2 to more suitably manage the working environment in the selective region Z1. Note that the controller 31 of the management device 3 is capable of controlling the second screen S2 to switch from the second screen S2a to the second screen S2b, in response to, for example, an instruction inputted by the manager M2 via the input device 36.

In a case where that manager M2 selects the selective region Z2 near the facilities O4 on the map Ma displayed by the output device 37, a transition to the third screen S3 illustrated in FIG. 8 occurs. According to FIG. 8, the safety and the amenity in the selective region Z2 are displayed with use of the amenity meter. This allows the manager M2 to more suitably understand the safety and the amenity in the selective region Z2, which is a narrow region.

Note that according to the above example, the map Ma is a map that shows the spatial distribution of the latest measurement values in the workplace A5 (the latest spatial distribution of the hazardous substance). In Embodiment 1, the management device 3 can alternatively make the map that shows the spatial distribution of the measurement values (the spatial distribution of the hazardous substance) with reference to, for example, the concentration of the dust and the positional information during a predetermined time period.

Note also that, according to the above example, management classes are discernibly displayed on the map Ma with use of numerical values represented by I through III. In Embodiment 1, no management class can be alternatively displayed on the map Ma. In a case where the management classes are displayed on the map Ma, the management classes can be displayed in any form, provided that the management classes are discernibly displayed. Note also that, according to the above example, the management classes are classified into three stages. In Embodiment 1, the management classes can be alternatively classified into any stages.

Note also that, according to the above example, on the second screen S2b on the right side of FIG. 7, the graph that shows the temporal changes in concentration of the dust, temperature, and humidity in the selective region Z1 on the map Ma is displayed. In Embodiment 1, on the second screen S2b, values of pieces of data detected by the various sensors such as the light sensor 21c and the sound sensor 21d can be alternatively displayed in addition to or instead of the temperature and the humidity. This allows the manager M2 to easily recognize correlation between the concentration of the dust and various pieces of data detected by the various sensors. As a result, it is possible for the manager M2 to more suitably manage the working environment in the selective region Z1.

Note also that, according to the above example, as illustrated in FIG. 8, each selective region, such as the selective regions Z1 and Z2, on the map Ma functions as an UI element for causing a transition to the third screen S3 on which the amenity meter that shows the safety and the amenity is displayed based on the concentration of the dust, a concentration of a gas (VOC), a illuminance, a noise, a degree of comfort, and a wet bulb globe temperature (WBGT). Note, however, that, in Embodiment 1, the map Ma is not limited to such a configuration.

Note also that the controller 31 of the management device 3 can control warning (alarm) to be displayed on the first screen S1 illustrated in FIG. 6, the warning indicating that the concentration of the dust in any of the unit workplaces A6 has increased, in a case where the concentration of the dust in the any of the unit workplaces A6 has increased. For example, the controller 31 of the management device 3 can control a caution to be displayed on the first screen S1 illustrated in FIG. 6, when the average or the maximum value of the concentration of the dust in any of the unit workplaces A6 reaches 80% of the management concentration, which is a predetermined management concentration corresponding to free silicic acid. Further, the controller 31 of the management device 3 can control a warning (alarm) to be displayed on the first screen S1, when (at the moment) the average or the maximum value of the concentration of the dust in any of the unit workplaces A6 reaches the management concentration. By thus sending a notification (for example, by displaying the caution or the warning) indicating that the concentration of the dust has increased in the any of the unit workplaces A6, it is possible for the manager M2 to more suitably manage the working environment in the any of the unit workplaces A6. Furthermore, by thus displaying the caution at a time point when the average or the maximum value of the concentration of the dust in the any of the unit workplaces A6 reaches 80% of the management concentration, it is possible to send, in advance, a notification indicating that the concentration of the dust has increased.

Moreover, the controller 31 of the management device 3 can predict a change in concentration of the dust with reference to correlation between (i) a measurement value that has been previously obtained in a measuring process (previous measurement value) and (ii) a measurement value that has been newly obtained in the measuring process. For example, the controller 31 of the management device 3 can predict the change in concentration of the dust as follows. That is, the controller 31 of the management device 3 extracts a measurement value that is highly correlative with the measurement value that has been newly obtained in the measuring process, from previous measurement values that have been obtained at predetermined measurement points A3 and the like illustrated in FIG. 1. The controller 31 of the management device 3 then predicts the change in concentration of the dust, with reference to how much the measurement value that has been newly obtained changes from such an extracted previous measurement value. This makes it possible for the manager M2 to more suitably manage the working environment in each of the unit workplaces A6.

(Example Display 2 of Map that Shows Spatial Distribution of Measurement Values in Workplace)

Figure 9:
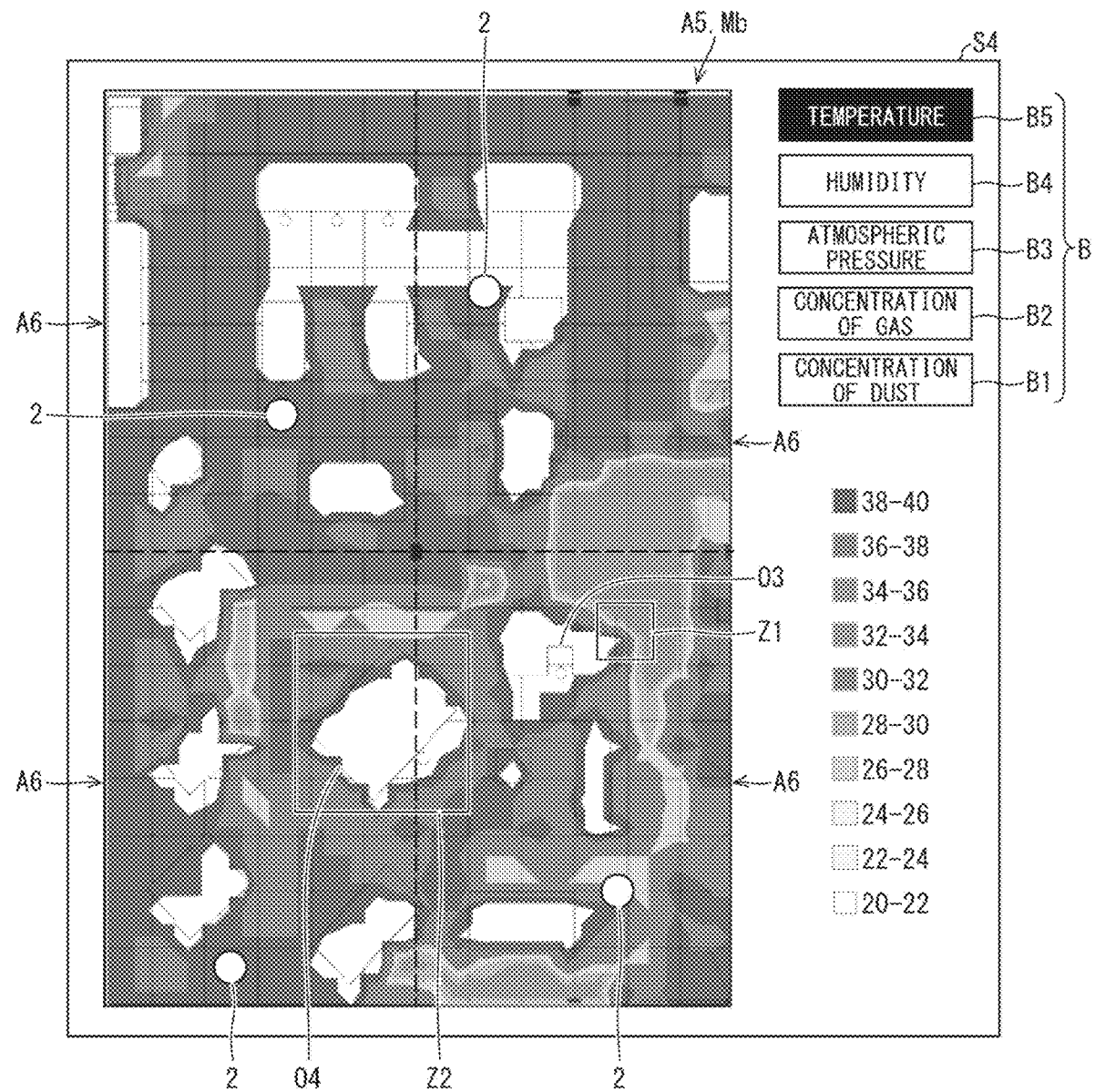
FIG. 9 is a drawing illustrating an example of a screen on which a map that is made in Embodiment 1 of the present invention and that shows spatial distribution of measurement values in the workplace is displayed.

Next, example display 2 of the map that shows the spatial distribution of the measurement values in the workplace will be described with reference to FIG. 9. FIG. 9 is a drawing illustrating an example of a screen (fourth screen S4) on which a map Mb that is made in Embodiment 1 of the present invention and that shows spatial distribution of measurement values (spatial distribution of a temperature) in the workplace A5 is displayed.

According to the map Mb illustrated in FIG. 9, out of the buttons B which are constituted by the buttons B1 through B5, the button B5 which is related to a temperature is selected, and temperatures ranging from 20° C. to 40° C. are discernibly displayed in 10 stages. The map Mb shows the spatial distribution of the measurement values of the temperature in the workplace A5 in a case where, in the step S103 illustrated in FIG. 3, each of the mobile devices 2 carries out the environment measurement with use of a temperature and humidity sensor 21e. This makes it possible to intuitively understand the condition of the workplace A5 which is a large region including the unit workplaces A6. Furthermore, the map Mb shows the mobile devices 2, the material storage O3, and the facilities O4, similarly to the map Ma. Since the mobile devices 2 are thus displayed on the map Mb, it is possible for the manager M2 to suitably manage the workers M1 who wear the respective mobile devices 2, as with the map Ma that shows the spatial distribution of the hazardous substance. Note that, according to the above example, the temperatures ranging from 20° C. to 40° C. are displayed in 10 stages on the map Mb. However, in Embodiment 1, the map Mb is not limited to such a configuration. In Embodiment 1, it is possible for the manager M2 to set a temperature range and the number of stages as desired depending on an environment of the workplace A5.

Note that it is possible for the manager M2 to switch display from the map Ma illustrated in FIG. 6 to the map Mb illustrated in FIG. 9, by selecting, via, for example, the input device 36, the button B5 related to the temperature, in a state where the button B1 related to the concentration of the dust is selected. Note also that selective regions, such as the selective regions Z1 and Z2, which function as UI elements for causing transitions to the second screen S2 and the third screen S3 can be displayed on the map Mb, as with the map Ma.

[Software Implementation Example]

Control blocks of the mobile device 2 and the management device 3 (particularly, the controllers 22 and 31) can be realized by a logic circuit (hardware) provided in an integrated circuit (IC chip) or the like or can be alternatively realized by software.

In the latter case, the mobile device 2 and the management device 3 each include a computer that executes instructions of a program that is software realizing the foregoing functions. The computer, for example, includes at least one processor and a computer-readable storage medium in which the program is stored. An object of the present invention can be attained by the processor of the computer reading and executing the program stored in the storage medium. Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. Further, the program may be supplied to or made available to the computer via any transmission medium (such as a communication network and a broadcast wave) which allows the program to be transmitted. Note that an aspect of the present invention can also be achieved in the form of a computer data signal in which the program is embodied via electronic transmission and which is embedded in a carrier wave.

The present invention is not limited to the embodiments, but can be altered by a skilled person in the art within the scope of the claims. The present invention also encompasses, in its technical scope, any embodiment derived by combining technical means disclosed in differing embodiments.

[Recapitulation]

A management method in accordance with an aspect of the present invention is a method for managing a working environment of a worker who moves in a workplace, including: a receiving process of receiving, from a mobile device worn by the worker, (i) a measurement value that has been obtained in a measuring process of carrying out environment measurement and (ii) positional information indicative of a location at which the measuring process has been carried out; and a making process of making, with reference to the measurement value and the positional information, a map that shows spatial distribution of measurement values in the workplace.

According to the above configuration, the mobile device worn by the worker who moves in the workplace carries out the environment measurement. With reference to the measurement value and the positional information received from the mobile device, the map that shows the spatial distribution of the measurement values in the workplace is made. Therefore, it is possible to suitably manage the working environment of the worker who moves in the workplace, as compared with a configuration in which a robot is used to carry out the environment measurement as in the technique disclosed in each of Patent Literatures 1 and 2 and a configuration in which a vehicle is used to carry out the environment measurement as in the technique disclosed in Patent Literature 3.

The management method in accordance with an aspect of the present invention is preferably arranged such that the workplace includes unit workplaces; and a management class of each of the unit workplaces is discernibly displayed on the map.

According to the above configuration, the management class of each of the unit workplaces included in the workplace is discernibly displayed on the map. This makes it possible to more suitably manage the working environment of the worker who moves in the workplace, by checking the management class of each of the unit workplaces.

The management method in accordance with an aspect of the present invention is preferably arranged such that the measurement value indicates a concentration of dust which concentration is measured with use of a dust sensor; and the making process includes a management class identifying process of identifying the management class of the each of the unit workplaces by comparing (i) an average or a maximum value of the measurement values that have been obtained by the environment measurement on a hazardous substance in the each of the unit workplaces with (ii) a management concentration that is a predetermined concentration corresponding to the hazardous substance.

According to the above configuration, it is possible to suitably identify the management class of each of the unit workplaces by comparing, with the management concentration, the average or the maximum value of the concentration of the dust which concentration is measured with use of the dust sensor, without an expert carrying out the environment measurement and analyzing data. This makes it possible to more suitably manage the working environment of the worker who moves in the workplace which contains the hazardous substance.

The management method in accordance with an aspect of the present invention is preferably arranged such that the hazardous substance is free silicic acid.

According to the above configuration, it is possible to more suitably identify the management class of each of the unit workplaces by comparing the average or the maximum value of the concentration of the dust with the management concentration which is a predetermined concentration corresponding to free silicic acid. This makes it possible to more suitably manage the working environment of the worker who moves in the workplace which contains the hazardous substance such as free silicic acid.

The management method in accordance with an aspect of the present invention is preferably arranged such that the mobile device carries out the measuring process at the location that is a predetermined location in the workplace.

According to the above configuration, the mobile device worn by the worker definitely carries out the measuring process of carrying out the environment measurement, at the predetermined location in the workplace. This allows measurement locations (measurement points) to be less concentrated at a specific location. It is therefore possible for a management device that has received the measurement value and the positional information from the mobile device to suitably make the map that shows the spatial distribution of the measurement values in the workplace. As a result, it is possible to more suitably manage the working environment of the worker who moves in the workplace.

The management method in accordance with an aspect of the present invention is preferably arranged such that the mobile device carries out the measuring process; and the mobile device shortens intervals at which the mobile device carries out the measuring process, as a speed at which the worker moves becomes faster.

According to the above configuration, the mobile device shortens measurement intervals, in a case where a speed at which the worker moves (acceleration) is fast. In contrast, the mobile device lengthens the measurement intervals, in a case where the speed at which the worker moves (acceleration) is slow (for example, in a case where the worker hardly moves). This allows measurement locations to be less concentrated at a specific location. It is therefore possible for the management device that has received the measurement value and the positional information from the mobile device to suitably make the map that shows the spatial distribution of the measurement values in the workplace. As a result, it is possible to more suitably manage the working environment of the worker who moves in the workplace.

The management method in accordance with an aspect of the present invention is preferably arranged such that, in the making process, the map that shows the spatial distribution of the latest measurement values in the workplace is made.

According to the above configuration, since the map that shows the spatial distribution of the latest measurement values in the workplace is made, it is possible to more suitably manage the working environment of the worker who moves in the workplace.

The management method in accordance with an aspect of the present invention is preferably arranged such that every time (i) the measurement value that has been newly obtained in the measuring process and (ii) the positional information indicative of the location at which the measuring process has been newly carried out are received from the mobile device in the receiving process, the map in which one of the measurement values which one corresponds to, in the map, the location at which the measuring process has been newly carried out is replaced with the measurement value that has been newly obtained in the measuring process is made in the making process.

According to the above configuration, it is possible to more suitably make the map that shows the spatial distribution of the latest measurement values in the workplace. This makes it possible to more suitably manage the working environment of the worker who moves in the workplace.

The management device in accordance with an aspect of the present invention is a management device which manages a working environment of a worker who moves in a workplace, including a controller, the controller carrying out each process included in the management method.

According to the above configuration, it is possible to bring about effects similar to those brought about by the management method.

The management device in accordance with an aspect of the present invention can be arranged such that the controller includes a processor and a memory; and the processor carries out the each process included in the management method, in accordance with a program stored in the memory.

According to the above configuration, it is possible to bring about effects similar to those brought about by the management method.

REFERENCE SIGNS LIST

1 Management system
2 Mobile device
3 Management device
21a Dust sensor
21b Acceleration sensor
21c Light sensor
21d Sound sensor
21e Temperature and humidity sensor
22, 31 Controller
23, 32 Main memory
24, 33 Auxiliary memory
25a, 25b, 34 Communication interface
L LAN
Wa, Wb WAN
23, 35 Input-output interface
27, 36 Input device
28, 37 Output device
29, 38 Bus
A1, A5 Workplace
A2, A6 Unit workplace
A3 Measurement point
A4 Initial location
B transmitter of a beacon (radio beacon)
M1 Worker
M2 Manager
Ma, Mb Map
O1, O3 Material storage
O2, O4 Facilities
P1, P2 Program
R Management room
S1 First screen
S2, S2a, S2b Second screen
S3 Third screen
Z1, Z2 Selective region

The invention claimed is:

1. A method for managing a working environment of a worker who moves in a workplace, comprising:
    a receiving process of receiving, from a mobile device worn by the worker, (i) a measurement value that has been obtained in a measuring process of carrying out environment measurement and (ii) positional information indicative of a location at which the measuring process has been carried out;
    a making process of making, with reference to the measurement value and the positional information, a map that shows spatial distribution of measurement values in the workplace, wherein:
    the workplace includes unit workplaces; and
    a management class of each of the unit workplaces is discernibly displayed on the map.

2. The method as set forth in claim 1, wherein:
    the measurement value indicates a concentration of dust which concentration is measured with use of a dust sensor; and
    the making process includes a management class identifying process of identifying the management class of the each of the unit workplaces by comparing (i) an average or a maximum value of the measurement values that have been obtained by the environment measurement on a hazardous substance in the each of the unit workplaces with (ii) a management concentration that is a predetermined concentration corresponding to the hazardous substance.

3. The method as set forth in claim 2, wherein the hazardous substance is free silicic acid.

4. The method as set forth in claim 1, wherein the mobile device carries out the measuring process at the location that is a predetermined location in the workplace.

5. The method as set forth in claim 1, wherein:
    the mobile device carries out the measuring process; and
    the mobile device shortens intervals at which the mobile device carries out the measuring process, as a speed at which the worker moves becomes faster.

6. The method as set forth in claim 1, wherein, in the making process, the map that shows the spatial distribution of the latest measurement values in the workplace is made.

7. The method as set forth in claim 6, wherein every time (i) the measurement value that has been newly obtained in the measuring process and (ii) the positional information indicative of the location at which the measuring process has been newly carried out are received from the mobile device in the receiving process, the map in which one of the measurement values which one corresponds to, in the map, the location at which the measuring process has been newly carried out is replaced with the measurement value that has been newly obtained in the measuring process is made in the making process.

8. A management device which manages a working environment of a worker who moves in a workplace, comprising a controller,
    the controller carrying out each process included in the method recited in claim 1.

9. The management device as set forth in claim 8, wherein: the controller includes a processor and a memory; and
    the processor carries out the each process included in the method, in accordance with a program stored in the memory.

* * * * *